(12) United States Patent
Orrock et al.

(10) Patent No.: US 7,231,324 B2
(45) Date of Patent: Jun. 12, 2007

(54) TECHNIQUES FOR ANALYZING DATA GENERATED BY INSTRUMENTS

(75) Inventors: James Orrock, Eden Prairie, MN (US); Thomas Larson, San Mateo, CA (US); Bruno Schueler, San Jose, CA (US); Lawrence Bot, Maple Grove, MN (US); James Quigley, Mountain View, CA (US); Emir Gurer, Scotts Valley, CA (US)

(73) Assignee: ReVera Incorporated, Sunnyvale, CA (US)

( * ) Notice: Subject to any disclaimer, the term of this patent is extended or adjusted under 35 U.S.C. 154(b) by 76 days.

(21) Appl. No.: 11/118,683

(22) Filed: Apr. 29, 2005

(65) Prior Publication Data

US 2006/0247899 A1 Nov. 2, 2006

(51) Int. Cl.
G06F 15/00 (2006.01)
(52) U.S. Cl. ............................ 702/189; 702/182
(58) Field of Classification Search ............... 702/189, 702/182; 205/305
See application file for complete search history.

(56) References Cited

U.S. PATENT DOCUMENTS

| | | | | |
|---|---|---|---|---|
| 4,492,740 A | * | 1/1985 | Yamamoto et al. | 428/629 |
| 5,995,916 A | * | 11/1999 | Nixon et al. | 702/182 |
| 6,326,617 B1 | * | 12/2001 | Tomie et al. | 250/305 |
| 2005/0092920 A1 | * | 5/2005 | Lee et al. | 250/305 |

* cited by examiner

Primary Examiner—John Barlow
Assistant Examiner—Xiuqin Sun
(74) Attorney, Agent, or Firm—Blakely, Sokoloff, Taylor & Zafman LLP

(57) ABSTRACT

According to one embodiment of the invention, a method for analyzing data from an instrument is disclosed. The raw data generated by the instrument, along with configuration data generated by a user, is packaged into a calling model. The raw data may include, for example, counts having a certain kinetic energy when analyzing photoelectron spectroscopy data. The configuration data may include several parameters selected by the user based on the composition and configuration of the structure being measured. The calling model may serve as an interface between the instrument and an engine for generating an algorithm for returning desired results to the user. The engine then generates the algorithm as well as the results specified by the user, and the calling model returns the results to the user. This allows a specific algorithm and results for a specific measured sample or structure to be generated using known algorithms and functions.

24 Claims, 15 Drawing Sheets

554

TECHNIQUES FOR ANALYZING DATA GENERATED BY INSTRUMENTS

NOTICE OF COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention generally relates to scientific instrumentation, and specifically to techniques for analyzing data generated by scientific instrumentation.

BACKGROUND

Scientific instruments, such as spectrometers, collect raw data (for example, in the form of a number of counts per second) that can be used to determine characteristics of a measured sample. The raw data needs to be processed to provide useful calculated results. Algorithms are therefore developed, as needed, to analyze raw data generated by instruments. The algorithms are typically developed by engineers who develop the instruments, and often require several months to develop.

Photoelectron spectroscopy is a technique used to determine the composition, thickness, profile, and etc. of elemental species in a sample. Photoelectron spectroscopy measures photoelectrons that are emitted by a sample that has been bombarded by monochromatic sources of radiation. For example, the sample may be bombarded with x-ray or ultraviolet radiation having a specific, predetermined wavelength. When the individual atoms of the sample absorb the photons of the radiation, the atoms emit an electron having a kinetic energy (KE) characteristic of the atom. This electron is known as a photoelectron. The photon absorbed by the atom has an energy $e=hv$, where h is Planck's constant and v is the frequency of the photon. The photoelectron was once bound to the emitting atom. The binding energy (BE) of the photoelectron is the amount of energy required to strip the photoelectron from the atom. The KE measured by the equipment is the amount of energy the photoelectron has after being emitted. Because of the law of conservation of energy, it can be determined that $KE=hv-BE$. As the BE for an electron in an atom has a known value, if the wavelength of the photon striking the sample is known, the KE of an emitted photoelectron can identify the species of the atom.

The emitted photoelectrons can be counted using an electron energy analyzer. A spectrum plotting the number of photoelectrons counted at specific kinetic energies can be generated from the raw data. The spectrum can then be used to determine various characteristics of the sample, such as the chemical composition or the thickness.

Characteristics of the sample can be determined or calculated using the spectrum. However, in order to determine useful information about the sample, a specific algorithm for the specific sample and the desired characteristics must be formulated for each new sample and for each new set of characteristics to be determined. Developing the algorithms is often time-intensive and can retard the progress of analyzing the sample.

SUMMARY

According to one embodiment of the invention, a calling model is described. The calling model includes a model structure and an interface between a data acquisition module and an algorithm engine. The model structure stores raw data generated by an instrument, and configuration data generated by a user. The raw data may be, for example, counts generated using photoelectron spectroscopy. The configuration data specifies functions and techniques for processing the data. The algorithm engine uses the configuration data to generate an algorithm for processing the raw data. After generating the algorithm, the algorithm engine dynamically calculates the results desired by the user, and passes the results back to the data acquisition module. In this way, an algorithm for determining certain characteristics of a sample can easily be specified by a user and generated by an algorithm engine.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

According to one embodiment of the invention, a method for analyzing data from an instrument is disclosed. The raw data generated by the instrument, along with configuration data generated by a user, is packaged into a calling model. The raw data may include, for example, photoelectron counts having a certain kinetic energy when analyzing photoelectron spectroscopy data. The configuration data may include several parameters selected by the user based the composition and configuration of the structure being measured. Examples of parameters include which function to use when calculating values, correction factors, etc. The calling model may serve as an interface between the instruments and an engine for generating an algorithm for returning desired results to the user. The engine then generates the algorithm as well as the results specified by the user, and the calling model returns the results to the user. This allows a specific algorithm and results for a specific measured sample or structure to be generated using known algorithms and functions.

An elemental species refers to the chemical composition of a specific layer or substrate. For example, a hafnium oxide layer includes the elemental species of hafnium and oxygen. An electron species refers to an electron having a characteristic energy. A layer having a single material species may emit several different electron species. For example, a silicon substrate may emit two different characteristic electrons having different kinetic energies. One electron may be emitted from the 2p orbital of the silicon atom, while the other electron may be emitted from the 2s orbital of the silicon atom. An electron signal hereinafter refers to a stream of electrons belonging to a specific electron species. For example, the 'Hf4f signal' comprises the electrons emitted by the 4f orbital of hafnium. Many of the examples discussed below refer to photoelectrons, or electrons that are emitted when a layer is bombarded with photons. Each elemental species may emit one or more photoelectron species, which may comprise a photoelectron signal.

Figure 1A:
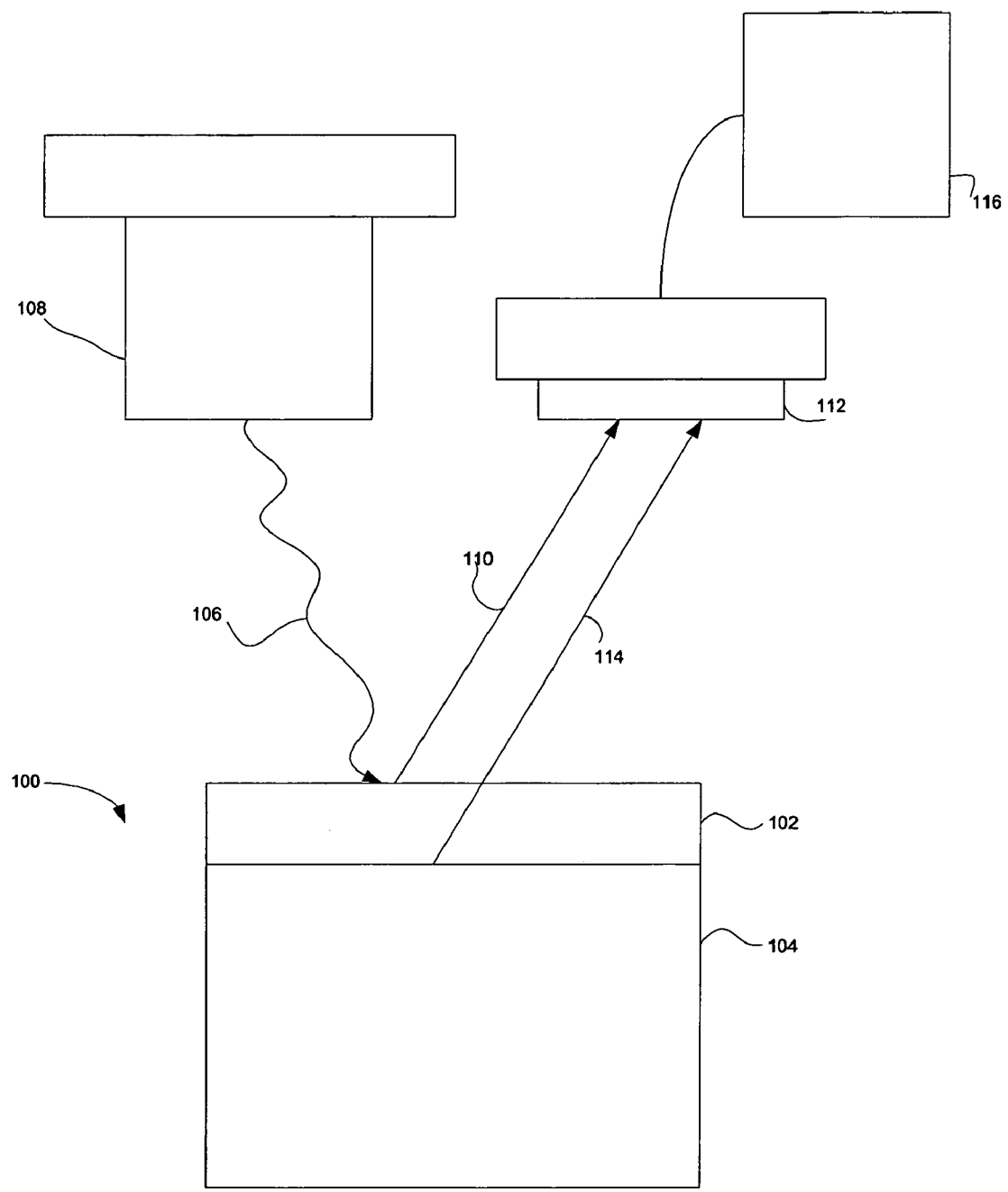
FIG. 1A illustrates a layered structure formed on a substrate according to one embodiment of the invention.

FIG. 1A illustrates a layered structure formed on a substrate according to one embodiment of the invention. FIG. 1A shows a structure 100 including a layer 102 formed on a silicon or other substrate 104 which may represent a portion of a larger micro-electronic device. Several characteristics of the layer 102 may be measured using X-Ray Photoelectron Spectroscopy (XPS) or similar techniques, such as Ultraviolet Photoelectron Spectroscopy (UPS), Auger spectroscopy, etc. For example, the thickness of the layer 102 or the atomic concentration (AC) of the layer 102, as well as the location of various species within the layer 102 (i.e., the profile) may be determined using these techniques. However, a unique algorithm must typically be generated for each calculation for each individual structure. Developing the algorithm is typically very time consuming.

The structure 100 includes the substrate 104 that forms the basis for the structure 100 and may be formed from single-crystal silicon. The layer 102 is formed over the substrate 104. The layer 102 in this example may be a Hafnium Oxide (HfO$_2$) layer. Although specific examples of elemental species are used here, it is understood that any layer material may be used with embodiments of this invention.

Using XPS or similar techniques, one may determine the thickness of the layer 102. In order to determine the thickness of the layer 102, the structure 100 is bombarded with x-ray wavelength photons 106 from an x-ray source 108 to stimulate the emission of a characteristic photoelectron using the photoelectric effect. The x-ray source 208 may include, for example, an electron gun to direct electrons at an anode to generate x-ray photons, and a lens to focus the x-ray photons on the structure 200. When a photon having a specific wavelength is absorbed by an atom in a molecule or solid, a core (inner shell) electron having a specific, characteristic energy for that species is emitted. The kinetic energy of the emitted photoelectrons can be used to determine the thickness, profile, dose, and other characteristics of the layer that generated them.

For example, the thickness of the layer 102 can be determined by taking a ratio of the intensities of two measured signals of photoelectrons emitted by the layer 102 and the substrate 104. A hafnium atom, when bombarded with x-ray wavelength photons, emits a characteristics photoelectron signal 110 comprising photoelectrons from the 4f orbital. The photoelectrons comprising the signal 110 have a characteristic kinetic energy that is measured and counted by an electron energy analyzer 112. The substrate 102 also emits a characteristic signal 114 comprising photoelectrons emitted by the silicon 2p orbital and influenced by the Si—Si bond (the "Si0" photoelectron). The signal 114 is also measured by the analyzer 112.

The analyzer 112 returns the measured results to a processing system 116. The processing system 116 may be a personal computer (PC) such as those having Intel® processors, and may interface with the analyzer 112 through a universal serial bus (USB) connection. The measured results are processed by the processing system 116 and returned to a user.

Figure 1B:
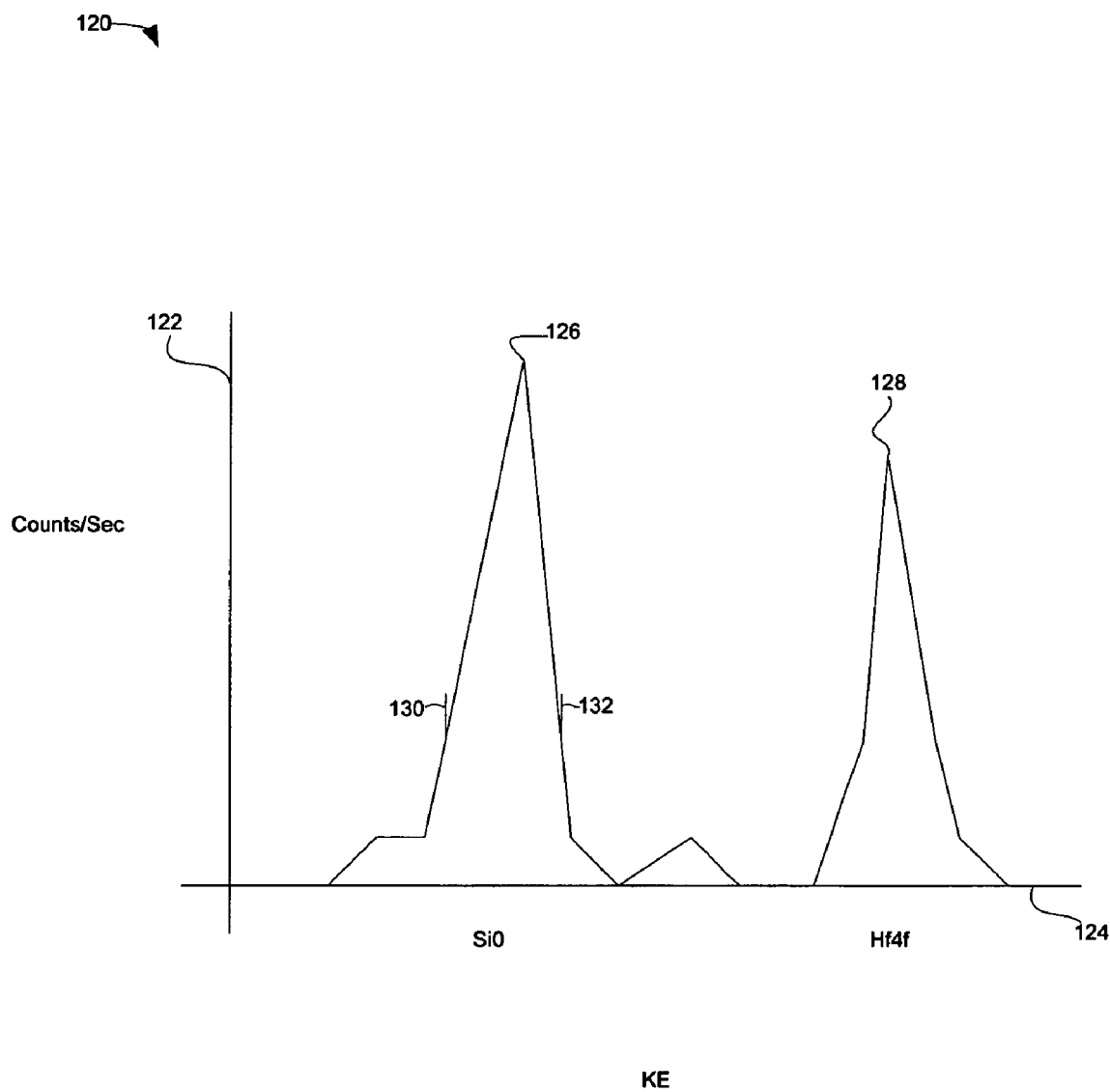
FIG. 1B illustrates a spectrum of the measured results generated by XPS spectroscopy.

FIG. 1B illustrates a spectrum 120 of the measured results generated by XPS spectroscopy. The spectrum 120 shows a number of counts per second measured along the y-axis 122, and a kinetic energy (KE) of the measured photoelectrons along the x-axis 124. The spectrum 120 shows two peaks, 126 and 128, corresponding to the measured signals 112 and 110, respectively. The number of counts as shown in the peaks 126 and 128 is used to determine the intensity of the signals 110 and 112. Configuration data, as will be explained below, is entered by the user to specify parameters for calculating layer thickness and other results. The parameters may specify an upper and a lower KE for counting a specific photoelectron species. For example, the peak 126 may have a lower bound 130 and an upper bound 132. The number of counts falling between these bounds determine the intensity of the SiO photoelectron species (i.e., more counts equals higher intensity), which is then used to determine the thickness of the layer 102. The peaks 126 and 128 may also be manipulated (e.g., shaped or fitted) or have background noise removed using standard techniques according to the configuration data as determined by the user. This configuration data is used to generate a unique algorithm for measuring characteristics of the structure 100.

Algorithms may be developed according to the parameters specified by the user. For example, the user may specify specific functions that are used to generate the algorithm. An algorithm to determine a thickness of a layer may include, for example, a ratio of two predictive intensity functions of emitted photoelectron species within a structure including the layer. The parameters specify which function to use for each photoelectron species. For example, a first photoelectron species may be emitted by a top layer, requiring a different intensity function than a second photoelectron species emitted by a layer beneath the top layer. The user can specify the specific function to use. Further, the peaks 126 and 128 may be reshaped or have background subtractions performed on them to accurately represent the intensity of the individual photoelectron signals. The user may also specify the bounds 130 and 132 shown above.

The intensities of photoelectrons characteristic to a layer (e.g., the layer 102) can be predicted using formulae that depend on the layer thickness and the attenuation of the signals in a film. Equation (1) can be used to determine the intensity of a signal that is not attenuated (i.e., a signal emitted by the top layer of a structure):

$$I(X_i) = I_{infXi} \cdot \left[1 - e^{\left(\frac{-t_x}{\lambda X i(X_i)}\right)}\right] \quad (1)$$

Where $X_i$ is the photoelectron species being measured, $I(X_i)$ is the intensity of the photoelectron signal, $I_{InfXi}$ is the intensity of a photoelectron signal emitted by a thick (i.e., greater than 10 nanometers (nm)) layer, $t_x$ is the thickness of the layer emitting the signal, and $\lambda_{Xi(X)}$ is the electron attenuation length (EAL) of the photoelectron species in a substrate X. An EAL is a measured quantity equal to the distance over which a photoelectron's original intensity drops to 1/e. EALs may be determined using, for example, the National Institute of Science and Technology's (NIST) EAL program. For example, the intensity of the signal 110 emitted by the layer 102 can be predicted using equation (1).

The intensity of the signal 114 emitted by the substrate 104 is attenuated by the layer 102, and therefore may be predicted using equation (2):

$$I(X) = I_{infX} \cdot \left[1 - e^{\left(\frac{-t_x}{\lambda_{X(X)}}\right)}\right] \cdot e^{\frac{-t_y}{\lambda_{X(Y)}}} \quad (2)$$

Where I(X) is the intensity of a photoelectron signal comprising a photoelectron species X and attenuated by an overlayer Y of thickness $t_y$, $\lambda_{X(Y)}$ is the EAL of photoelectrons emitted by the elemental species X in the layer Y, and $\lambda_{X(X)}$ is the EAL of photoelectrons emitted by the elemental species X in the layer X.

In order to determine the thickness of the layer 102, the ratio of the intensities of the two signals 110 and 114 is determined. A ratio is used because the specific intensities measured by the analyzer 112 change from measurement to measurement and depend on the x-ray wavelength used and other factors. The ratio of the intensities of the signals 110 and 114 may be given, for example, by equation (3):

$$\frac{I(SiO)}{I(Hf4f)} = \frac{I_{infSi} \cdot e^{\frac{-t_{Hf}}{\lambda_{si(HfO2)}}}}{I_{infHf} \cdot \left(1 - e^{\frac{-t_{Hf}}{\lambda_{Hf(HfO2)}}}\right)} \quad (3)$$

Equation (3) may be solved iteratively to determine the thickness $t_{Hf}$ using a program such as Matlab®. I(Hf4f) is the measured intensity of photoelectrons emitted by the 4f shell of hafnium (i.e., the signal 110 and the peak 128), while I(SiO) is the measured intensity of photoelectrons emitted by the substrate 102. $I_{(infHf)}$ and $I_{(infSi)}$ are the measured intensities of a photoelectron emitted by a thick (i.e., greater than 10 Angstroms) layer of hafnium oxide and silicon, respectively. $\lambda_{Si(HfO2)}$ and $\lambda_{Hf(HfO2)}$ are the measured electron attenuation lengths (EALs) of silicon and hafnium photoelectrons emitted by the substrate 104 and the layer 102. The intensity of the silicon signal 114 is attenuated by the layer 104. The equations (1) and (2) are examples of thickness functions that may be specified in the configuration data created by the user. The equation (3) is an algorithm generated by the process described below.

Other factors may be taken into account when determining a final algorithm used to determine the thickness of the various layers of the structure 100. For example, the intensity functions shown above may be tailored to fit different situations. Additionally, various ranges of collected energies may be used in determining the number of counts for a particular photoelectron. Other results may be also determined (e.g., atomic concentration (AC), profile (i.e., the position of the elemental species within the layer)).

The various parameters described above may be entered by a user, along with the raw data generated by the instrument, into a calling model to give the desired results back to the user. The calling model may pass the raw and configuration data to an engine to generate the results, and the calling model may also pass the results back to the user. According to one embodiment, the engine used to determine the results is a set of configurable functions implemented in Matlab®. However, it is understood that any engine capable of processing algorithms, such as a C++, FORTRAN 77, etc. interpreter.

Figure 2:
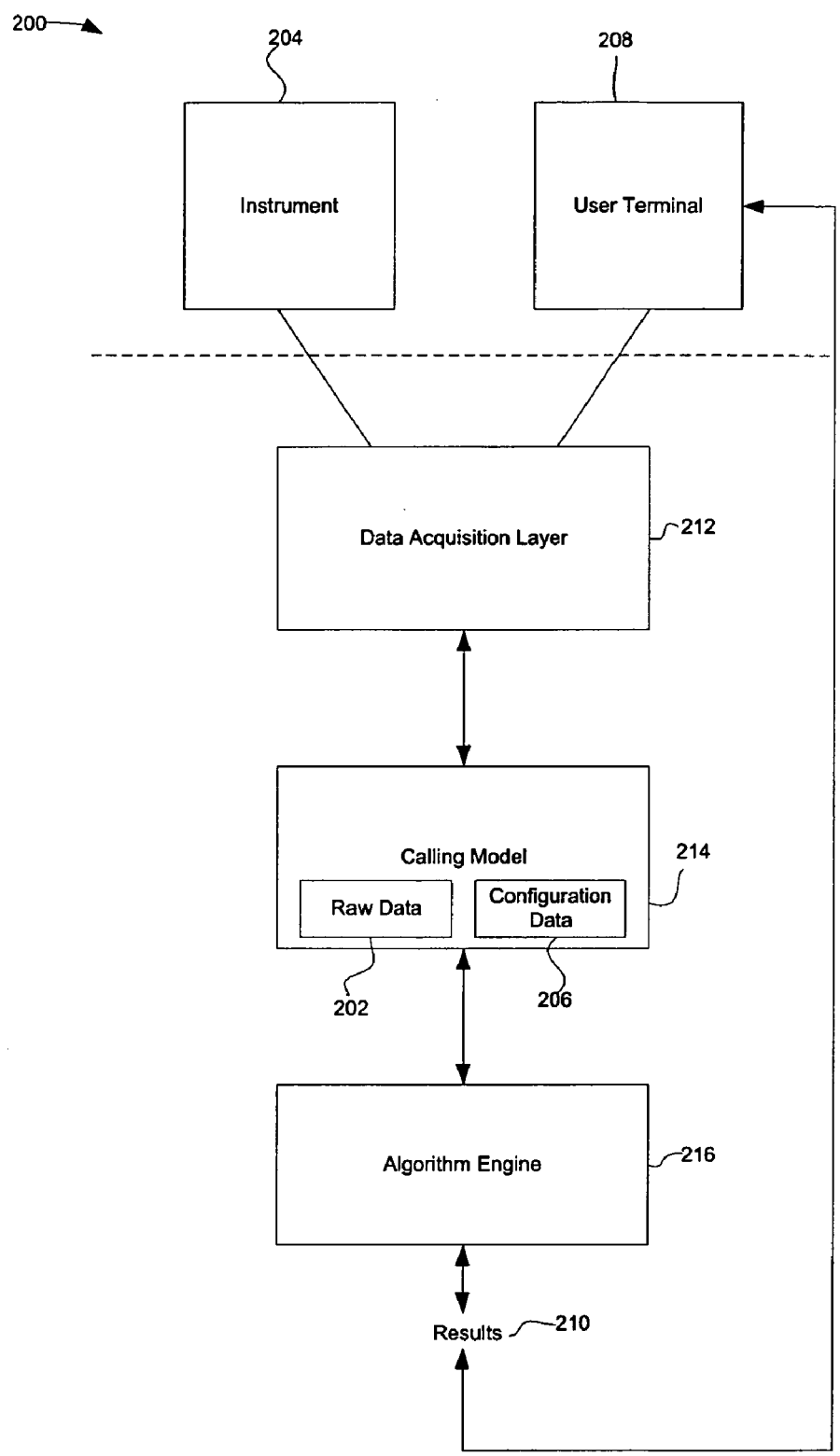
FIG. 2 is a diagram of the interaction between a calling model and other components of a system for generating results from data collected by an instrument.

FIG. 2 is a diagram of the interaction between a calling model and other components of a system for generating results from data collected by an instrument. The system 200 collects raw data 202 from an instrument 204 (such as the analyzer 112) and configuration data 206 from a user terminal 208. The user terminal 208 may include input and output devices to allow a user to input the configuration data 206 and receive results 210 of the calculations. The raw data 202 may be counts of a number of photoelectrons having a specific energy (as shown in FIG. 1B), or any other type of data generated by the instrument 204. The configuration data 206, as was described above, and will be described below in more detail regarding FIGS. 5A–5G, includes parameters entered by a user to generate a specific algorithm or algorithms to measure the characteristics desired by the user. It is understood that although specific examples of developing algorithms and calculating results are given, that any measured data requiring processing using a specific algorithm that may be developed using component algorithms or functions may be used with embodiments of the invention.

A data acquisition module 212 may include a graphical user interface (GUI) to collect the parameters comprising the configuration data 206 (as will be shown below), as well as any communications interface needed to collect data from the instrument 304. The raw data 202 and configuration data 206 is packaged into a calling model 214 (the specifics of the calling model 214 are shown below in FIG. 4). The calling model 214 includes a model structure that stores the raw data 202 and the configuration data 206.

The calling model 214 then passes the raw data 202 and the configuration data 206 to the algorithm engine 216. The algorithm engine 216 uses the configuration data to assemble a specific algorithm for measuring the desired characteristic of the structure or specimen being measured. The algorithm engine 216 then generates the results 210 which are returned to the calling model 214, and passed back to the user terminal 208 for the user to view.

The configuration data 206 is used by the algorithm engine 216 to formulate an algorithm for determining the specific characteristic(s) that the user wishes to calculate. For example, the configuration data may include settings to change the fit or shape of the peaks 126 and 128, determine boundaries of the peaks 126 and 128, functions to call to generate the algorithm, and other settings. Using the example shown above in Equation (3), for example, the configuration data 206 may specify that the photoelectron species being measured are photoelectrons emitted by the 4f orbital of hafnium oxide and photoelectrons emitted from the 2p orbital of silicon. The intensity functions may also be specified, noting that the signal 114 generated by the silicon substrate 104 is attenuated by the layer 102. The algorithm engine would determine that the equation (1) is used as a predictive intensity function for the signal 110, and that the equation (2) is used as a predictive intensity function for the signal 114 (since the signal 114 is emitted by the substrate 104 and is attenuated by the layer 102). The measured intensity data may be modified based on the fitting or background subtraction of the peaks 126 and 128. Equation (3) is the resulting algorithm that can be formed using the calling model 214. FIG. 3B describes an example of constructing an algorithm.

Figure 3A:
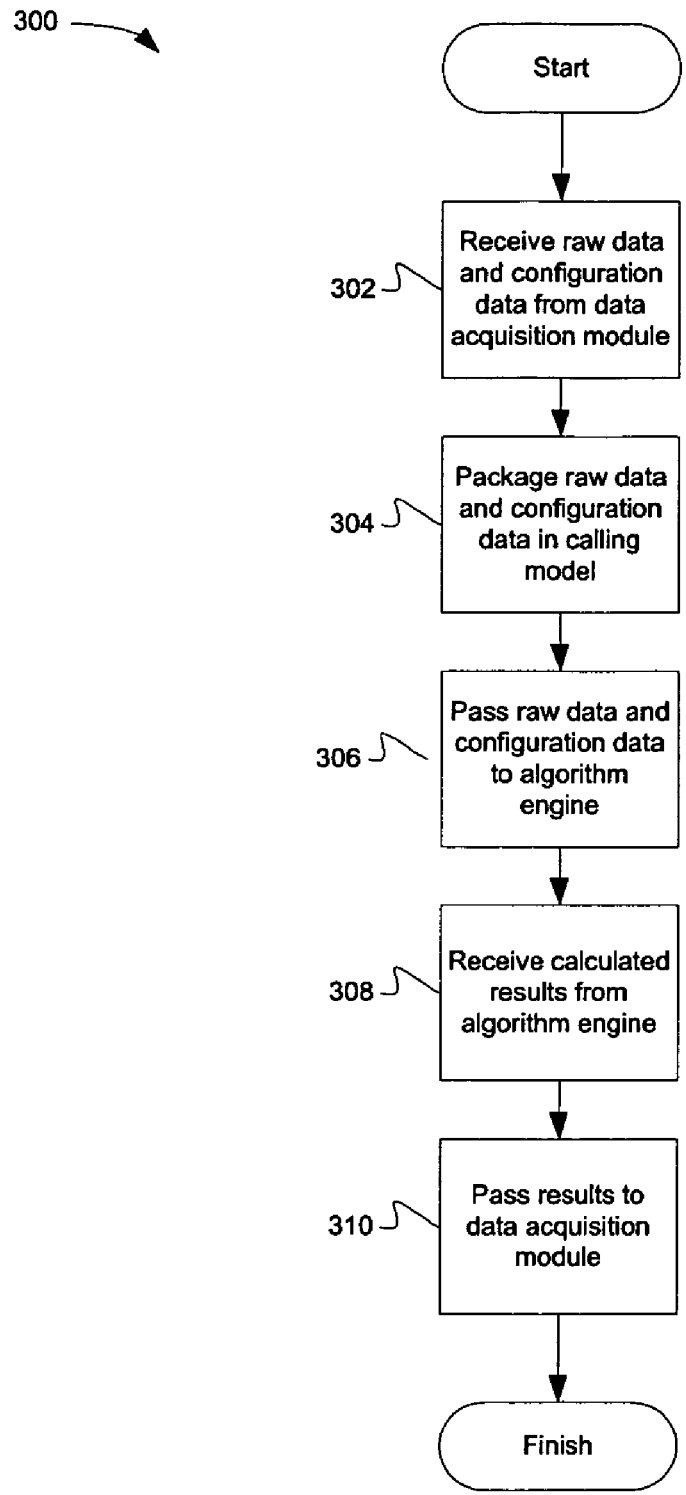
FIG. 3A is a flowchart describing a process for using a calling model to assemble an algorithm, process raw data, and return results to a user.
Figure 3B:
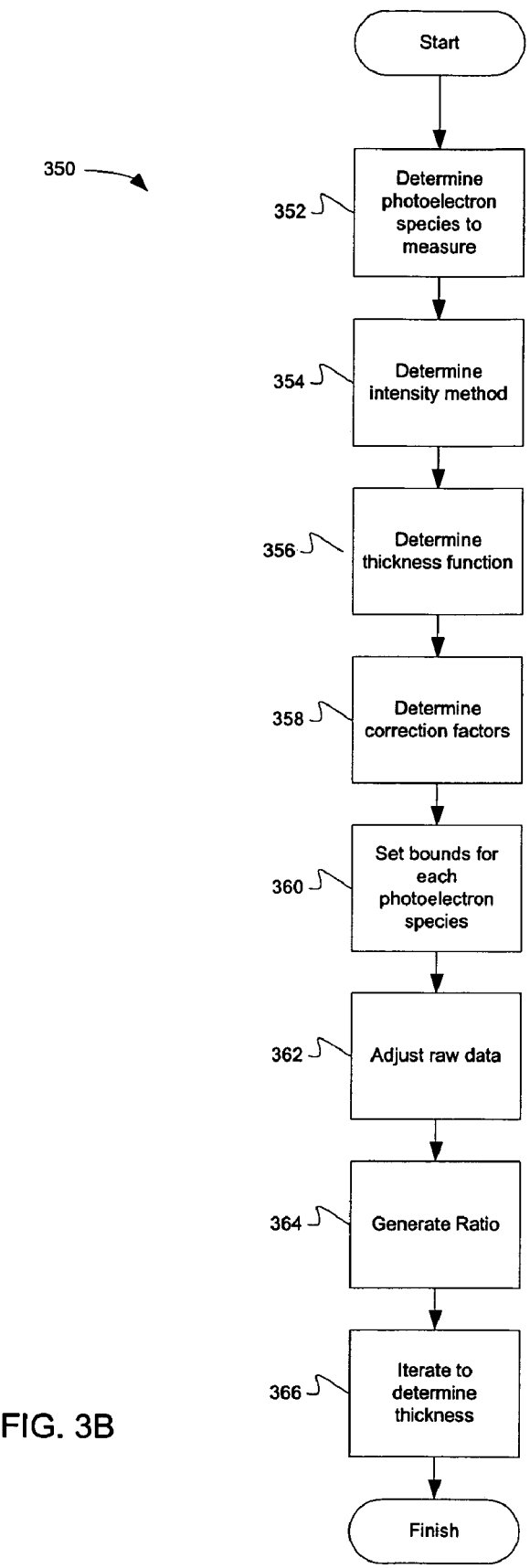
FIG. 3B is a flowchart describing a process for generating an algorithm according to one embodiment of the invention

FIG. 3A is a flowchart describing a process for using a calling model to assemble an algorithm and return it to a user. The process 300 is described from the perspective of the calling model 214. In block 302, the raw data 202 and configuration data 206 is received from the data acquisition module 212. In block 304, the raw data 202 and configuration data 206 are packaged into the calling model 214. The calling model 214 includes a model structure that will be described regarding FIG. 4.

In block 306, the calling model 214 passes the raw data 202 and the configuration data 206 to the algorithm engine 216. The algorithm engine 216 then computes the desired results based on the contents of the calling model 212. In block 308, the calling model 212 receives the calculated results 210 from the algorithm engine 216. The results 210 are then passed to the data acquisition module 212 in block 310. The user can then view the results 210 using the user terminal 208.

FIG. 3B is a flowchart describing a process for generating an algorithm according to one embodiment of the invention. The process 350 is an example of a process for determining an algorithm for determining a thickness of a layer, and may be used during block 308, above. The process 350 may occur in the algorithm engine 216. It is understood that other algorithms may be constructed in a similar manner.

In block 352, the photoelectron species to be measured are determined. For example, according to the parameters, a user may have chosen to measure the Hf4f species and the O species of a layer. In block 354, a method for shaping the intensity curve of each photoelectron species is determined. The method is specified in the parameters of the configuration data. The intensity method may be, for example, the "PeakArea" method, which may calculate an area of a peak in a region using simple integration. A different intensity method may be chosen for each peak 126 or 128. For example, the "PeakArea" method may be chosen for the peak 126, while the "PeakFit" method is chosen for the peak 128.

In block 356, a thickness function for each species is determined. The thickness function chosen may be similar to one of the equations (1) or (2) shown above. The user chooses the function based on the configuration of the structure being measured. In block 358, correction factors are determined. A user may have chosen one or more correction factors to adjust the measured data as necessary for equipment variations, etc. In block 360, the bounds are set for each photoelectron species. For example, an upper and lower energy bound may be set for each photoelectron species to determine which counts to include in the measured intensity for a specific species.

In block 362, the raw data is adjusted based on the correction factors, intensity functions, and bounds chosen above. Once the corrected raw data is determined, a measured intensity for each photoelectron species is known. In block 364, the ratio similar to the ratio of equation (3) is generated. The ratio is based on the thickness functions determined in block 356. In block 366, the ratio is iterated to determine the thickness of the layer. The thickness of the layer is among the results, and it is passed back to the user when calculated.

Figure 4:
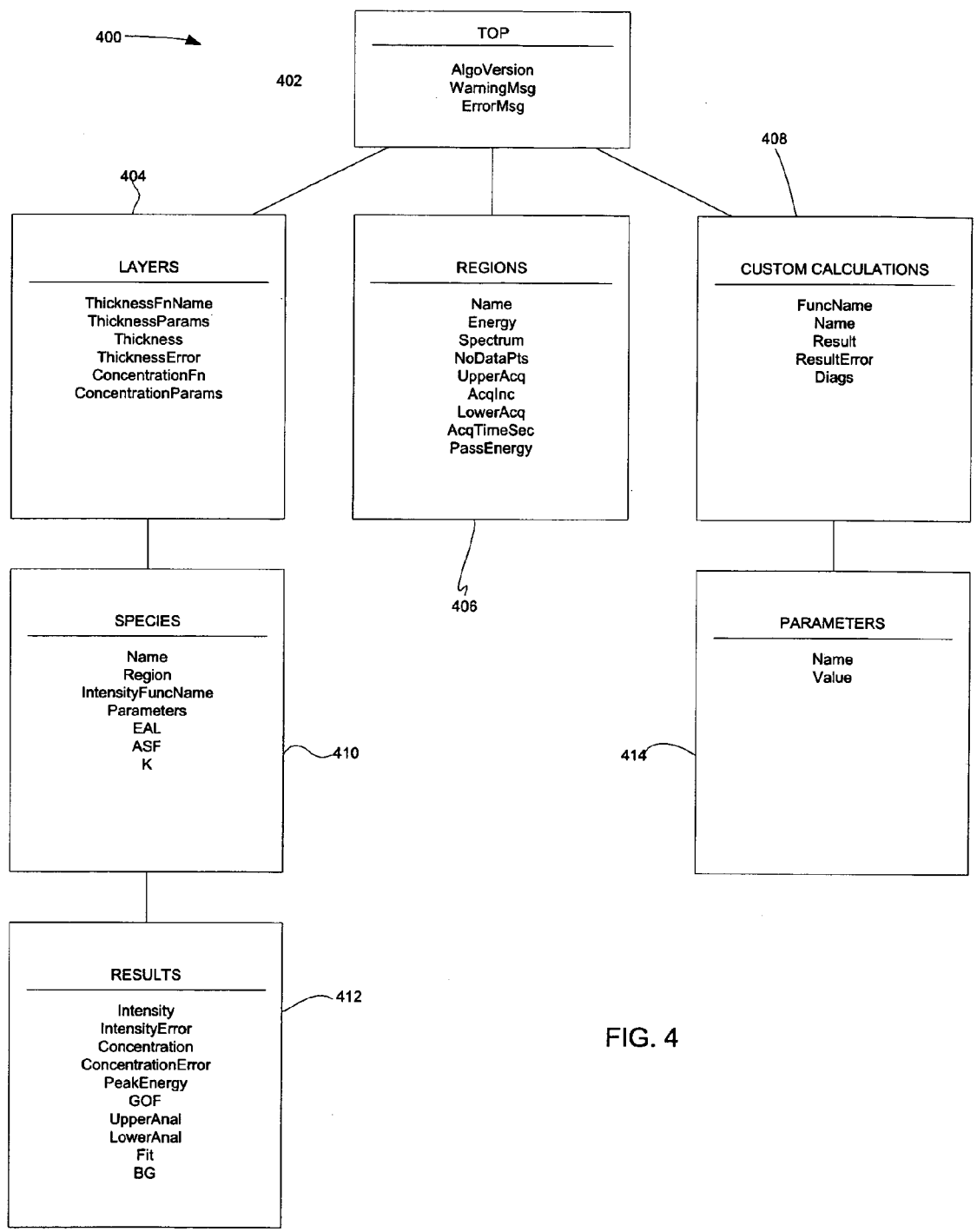
FIG. 4 is a schematic diagram of a model structure of the calling model according to one embodiment of the invention.

FIG. 4 is a schematic diagram of a model structure 400 of the calling model 212 according to one embodiment of the invention. The calling model 212 includes both a model structure 400 as well as an interface between the instrument interface layer 212 and the algorithm engine 216. The raw data 202 and the configuration 206 are embodied within the model structure 400.

The model structure 400 is a hierarchical environment that includes fields for the various parameters that can be set by the user (i.e., the configuration data 206), the raw (measured) data 202 generated by the instrument 204, and the results 210 generated by the algorithm engine 216. The model structure 400 is one way to implement the various embodiments of this invention, however, it is understood that other techniques and/or constructs may be used in its place. It is further understood that the following model structure 400 is an example, and that it may be tailored based on the application.

The model structure 400 includes a top list 402 that houses the other various lists of the model structure 400. The top list 402 includes a layers list 404, a regions list 406, and a custom calculations list 408. The top list 402 may also include fields for passing version data (AlgoVersion), as well as fields for the algorithm engine 216 to return warning (WarningMsg) and error messages (ErrorMsg). The layers list 404 includes another list, a species list 410, which in turn includes a results list 412. The custom calculations list 408 includes a parameters list 414.

The layers list 404 includes a number of parameters for each individual layer. For example, the layers list 404 may include the layer 102 shown in FIG. 1A. Additionally, in multi-layer structures, other layers may be included in the layers list 404. For each of the layers in the layers list 404, parameters (i.e., configuration data) and raw data are provided. For each layer, for example, a list of the various species within the layer is given (e.g., the species list 410). Also found in the layers list 404 (for each layer) is a thickness function to be used (ThicknessFnName), parameters required by the thickness function (ThicknessParams), and the resulting thickness (Thickness) and thickness error (ThicknessError, provided by the algorithm engine 216). Further, the layers list 404 may also include field for atomic concentration (AC) functions and parameters (ConcentrationFn and ConcentrationParams). The thickness functions and concentration functions are predetermined algorithms that can be used to assemble a thickness or concentration function for an entire structure. For example, predetermined thickness functions for measuring a single layer's thickness, the thickness of a layer in a two layer structure, and the thickness of a SiON (silicon bound to oxygen and nitrogen) layer may already be known to the algorithm engine 216. These known algorithms are combined with the other parameters to result in an overall algorithm for the structure being measured. The overall algorithm is used by the algorithm engine 216 to calculate the desired thicknesses.

The species list 410 includes data for each measured photoelectron species emitted by a particular layer. For example, for an Aluminum Oxide layer, two species of photoelectrons (a 2s and a 2p species) may be observed. For each photoelectron species, a name of the species (Name), a region of spectral data (see FIG. 1B) to observe the photoelectron species in (Region), an intensity function to describe the intensity of the photoelectron species (IntensityFuncName), parameters for the intensity function (Parameters), EALs, atomic sensitivity factor (ASF), and a bulk material intensity (k) for the species are provided. These parameters are used along with the thickness and concentration functions described above to provide the desired results. For example, as explained above regarding Equation (3), different intensity functions may be chosen based on the relative position of the layer containing the species within the structure.

The results list 412 includes the results of the calculations for each species found in the species list 410. For each species, a calculated intensity (Intensity) and intensity error (IntensityError), as well as a calculated AC (Concentration) and AC error (ConcentrationError) are returned. The results list 412 also includes the peak energy of the photoelectrons (PeakEnergy, i.e., the energy at which the most photoelectrons were counted for the particular species), the goodness of fit of the intensity calculation (GOF), the upper and lower bounds (UpperAnal and LowerAnal, e.g., the bounds 130 and 132) for the species used by the intensity function, and the fit (Fit) and background subtraction calculations (BG) used by the algorithm engine 216.

The regions list 406 includes a list of regions within the spectrum shown in FIG. 1B. The regions are defined in the list 406 to be used by when calculating results for certain layers and certain species. The regions list 406 includes a name for each region (Name), energy values measured for the spectrum (Energy), the count values for the spectrum (Spectrum, i.e., the raw data 202), the number of data points (NoDataPoints, i.e., the total number of counts), the upper and lower acquisition energies (UpperAcq and LowerAcq, i.e., the highest and lowest energies measured), the increment between bins (AcqInc, i.e., for each count, the range of energy values covered), an acquisition time for the spectrum (AcqTimeSec), and the pass energy for the spectral region (PassEnergy).

The custom calculations list 408 is used to define a calculation not otherwise defined in the model structure 400. For example, a user may calculate the profile (i.e., the location of a species within a layer) using a custom calculation. The custom calculations list 408 includes a function name called to evaluate the custom calculation (FuncName, this is the internal function used by the algorithm engine 216), a name for the custom calculation (Name), the result and result error of running the custom calculation (Result and ResultError). The parameters for the custom calculation include a parameters list 414. The parameters list, for each parameter, includes a parameter name (Name) and value (Value).

Figure 5A:
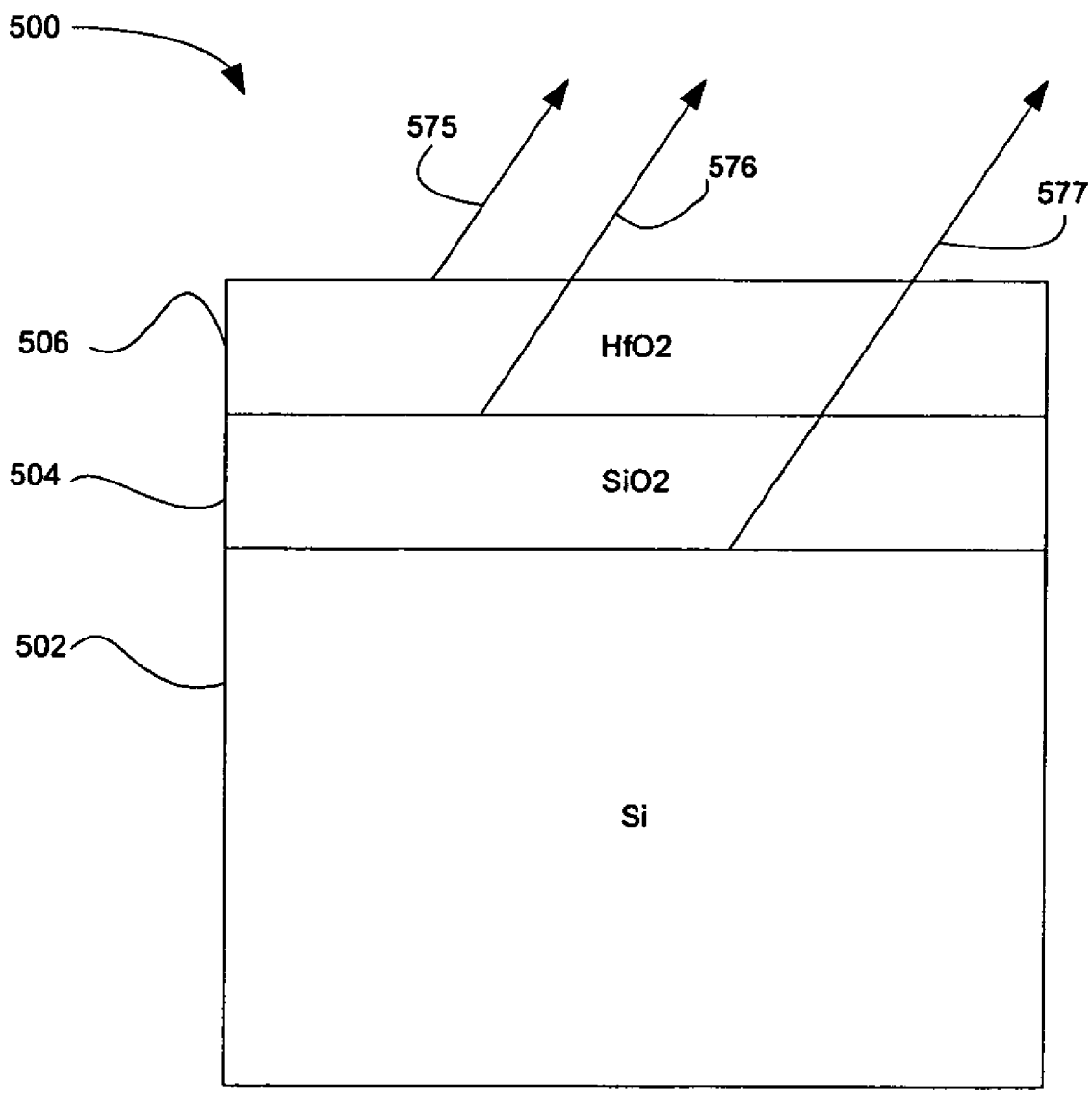
FIGS. 5A–5G illustrate an interface for inputting the configuration data according to certain embodiments of the invention.

FIGS. 5A–5G illustrate an interface for inputting the configuration data 206. A GUI may be used by the instrument interface layer to allow a user to specify the parameters that are inputted into the model structure 400. Although a GUI is described, it is understood that other input techniques, such as a command line interface (CLI) may be used. The specific example used here shows the parameters chosen to calculate a thickness and AC for a hafnium oxide layer over a silicon dioxide layer on a silicon substrate. FIG. 5A illustrates a structure 500 to be measured using XPS or a similar technology. The structure 500 includes a substrate 502, a silicon dioxide layer 504, and a hafnium oxide layer 506. FIGS. 5B–5G illustrate the interface for inputting parameters used to generate an algorithm to determine characteristics of the structure 500.

Figure 5B:
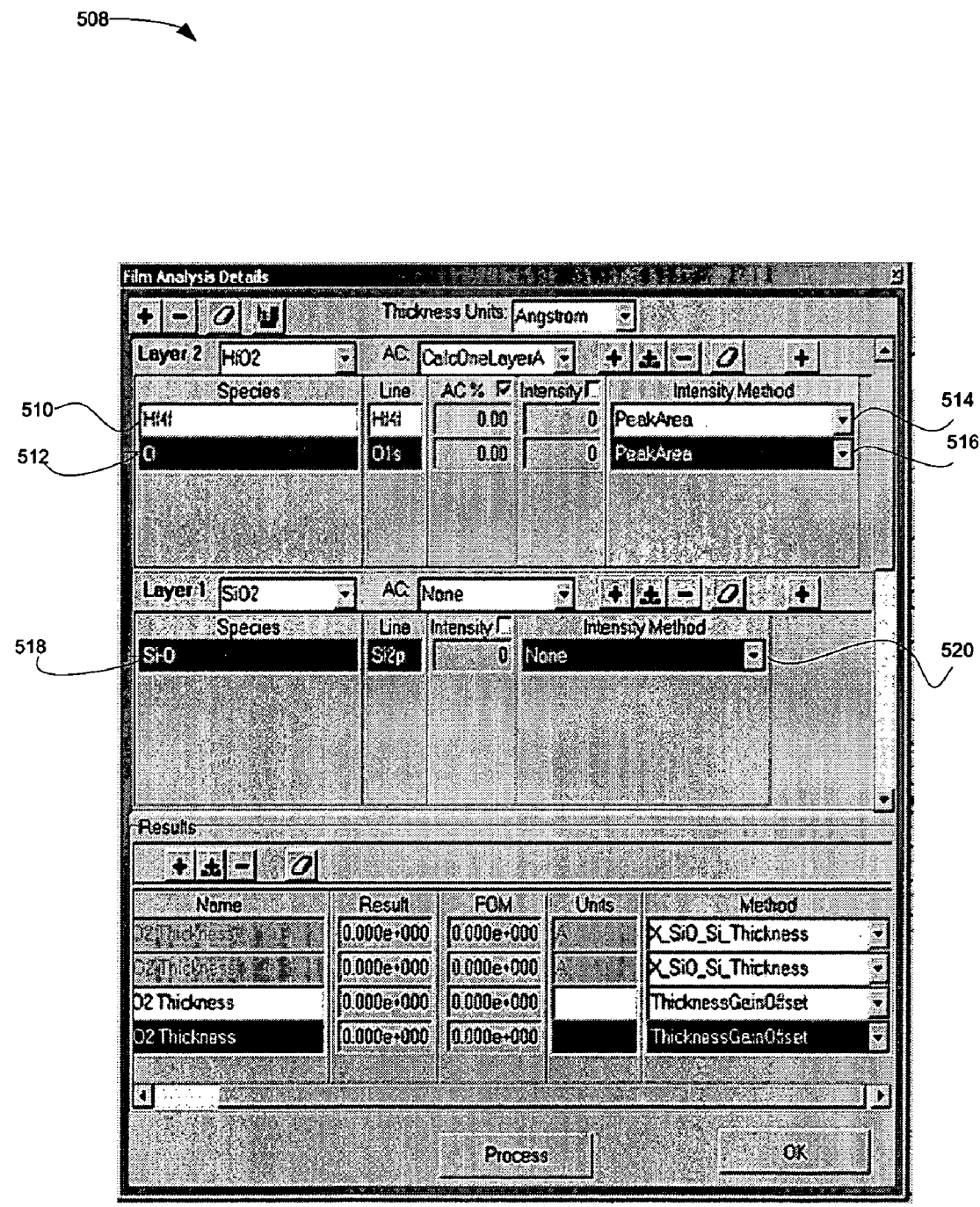

FIG. 5B shows a window 508 used to specify the intensity methods and other functions to be used. The windows 510 and 512 show the specific species of the hafnium oxide layer 506 that can be measured using the instrument 204. As shown, the hafnium oxide layer 506 may emit a Hf4f photoelectron as well as a 1s electron from the oxygen atom. The intensity method for shaping the peak of each of the photoelectron species is specified using the menus 514 and 516. According to another embodiment, the specific photoelectron species may also be chosen using the window 508. For example, as shown here, a PeakArea function is used to shape peaks of the Hf4f and O species. Other functions may also be used. A photoelectron species of the silicon dioxide layer (the Si—O species) can be specified in the window 518. A window 520 is used to select an intensity method for the Si—O species. No intensity method is chosen, which may result in a default intensity method (e.g., the PeakArea function) being used.

Figure 5C:
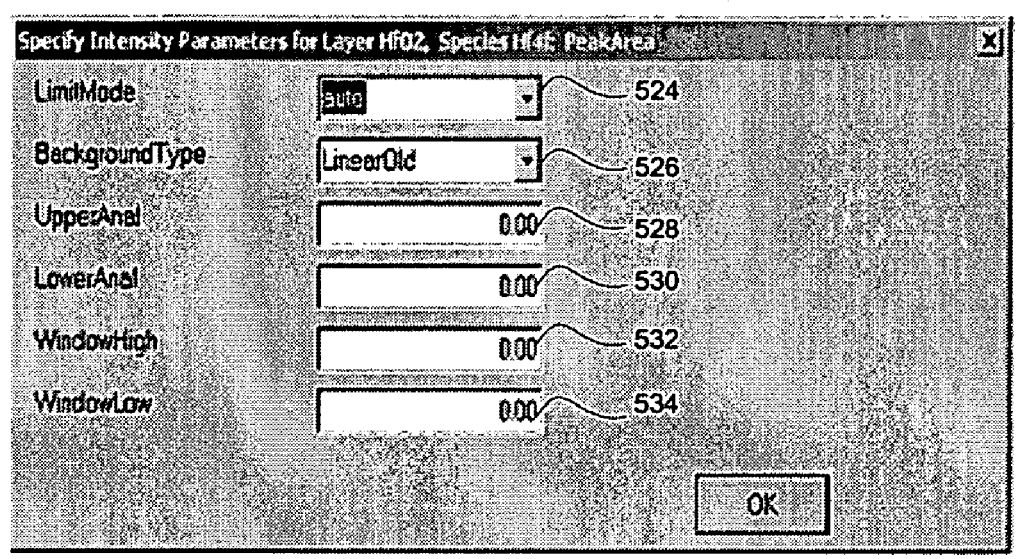

FIG. 5C illustrates a window 522 for specifying intensity parameters for the Hf4f species of the hafnium oxide layer 506. The menu 524 specifies the limit mode for the intensity function. The window 526 is used to choose the background subtraction used on the peak generated by the Hf4f species. The background subtraction is used to remove background noise from the spectrum. The windows 528 and 530 are used to specify the UpperAnal and LowerAnal limits for the photoelectron species. The UpperAnal and LowerAnal limits specify the upper and lower bounds 128 and 130 of FIG. 1B. The windows 532 and 534 are used to specify the WindowHigh and WindowLow parameters. The WindowHigh and WindowLow parameters may set bounds such as the bounds 130 and 132, but are measured from the middle of the peak (e.g, the peak 126 or the peak 128). Other windows similar to the window 522 may be used to specify similar parameters for the other species (e.g, the O species) of the layers 504 and 506.

Figure 5D:
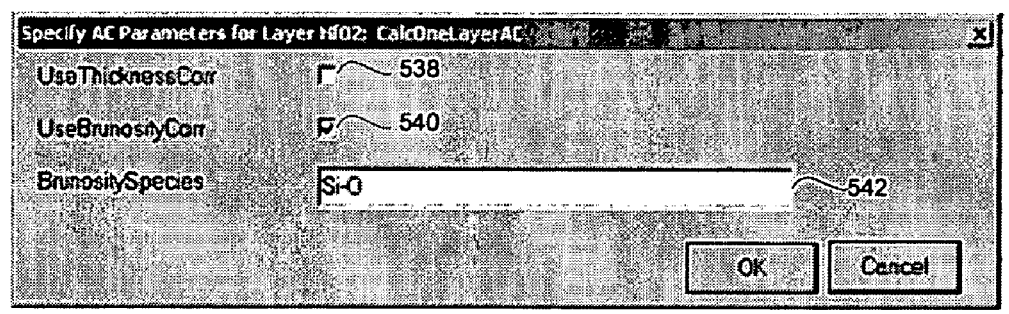

FIG. 5D illustrates a window 536 for inputting AC parameters for the hafnium oxide layer 506. A user may check the checkbox 538 to use the thickness correction. According to one embodiment, the algorithm engine 216 assumes a layer of infinite thickness when calculating AC. The thickness correction 538 may be chosen to indicate that the layer has a finite thickness. Likewise, a user may check the checkbox 540 to use the Brunosity correction. The Brunosity correction corrects for the fact that when you have interfacial silicon dioxide, often too many oxygen photoelectrons are counted. The Brunosity species (the photoelectron species to which the Brunosity correction is being applied) is specified in the window 542.

Figure 5E:
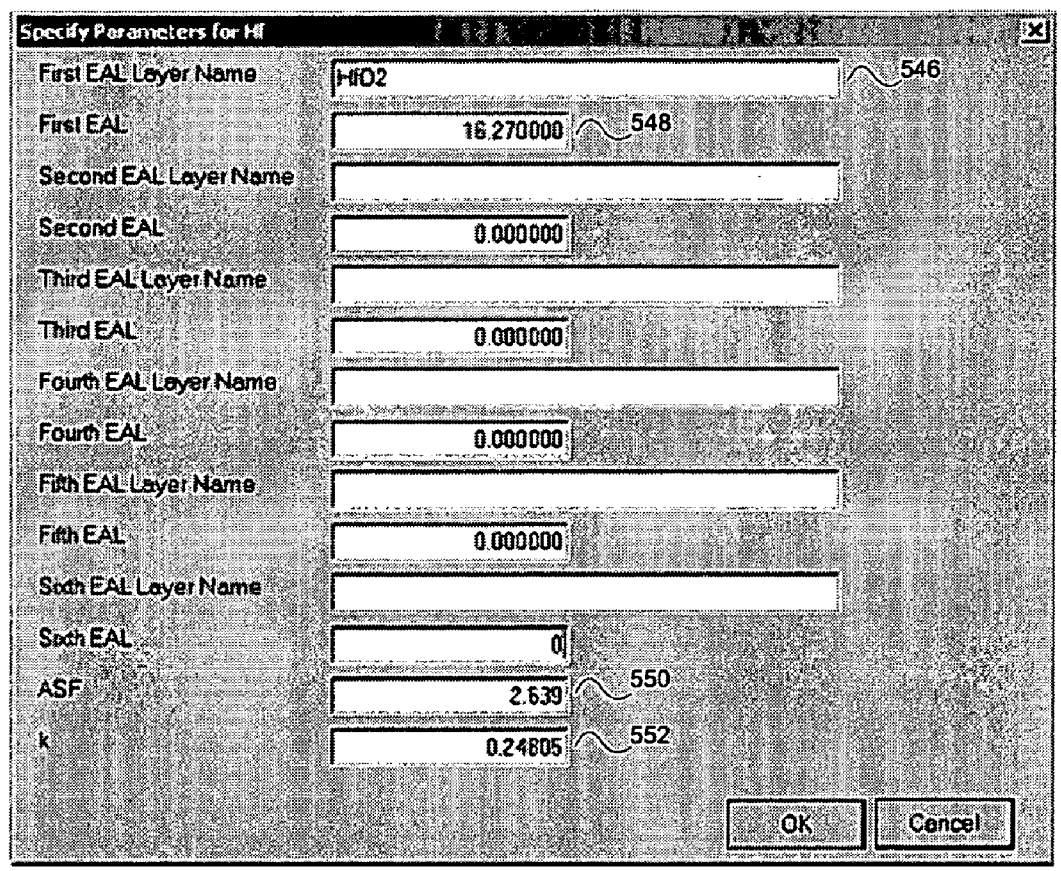

FIG. 5E illustrates a window 544 for inputting EALs and other parameters. The window 544 includes two windows 546 and 548 for inputting an EAL layer name and an EAL value for hafnium. The window 544 also includes a window 550 for inputting an ASF value for hafnium and a window 552 for inputting a bulk material intensity ("k") for hafnium.

Figure 5F:
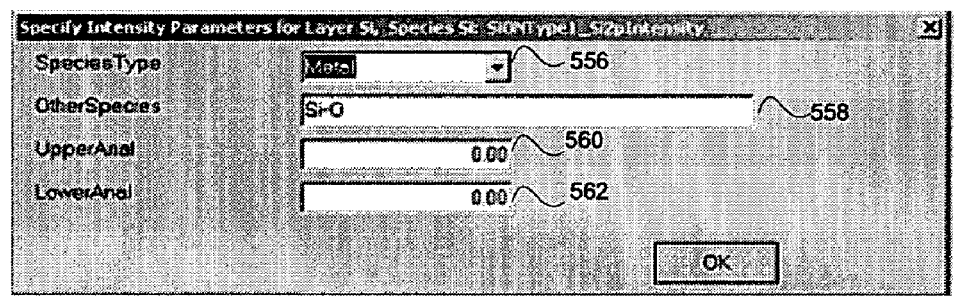

FIG. 5F illustrates a window 554 for inputting parameters for the intensity function SiONType1_Si2pIntensity. The function SiONType1_Si2pIntensity is one of the preset algorithms used to determine the intensity function of a signal emitted by the substrate 502. The menu 556 is used to choose the species type of the layer. According to one embodiment, the elemental species may either be an oxide or a metal. The window 558 is used to denote other species that may be found in the substrate 502. The windows 560 and 562 are used to specify the UpperAnal and LowerAnal parameters for the substrate 502. As mentioned above, the UpperAnal and LowerAnal parameters correspond to the bounds 128 and 130 shown in FIG. 1B.

Figure 5G:
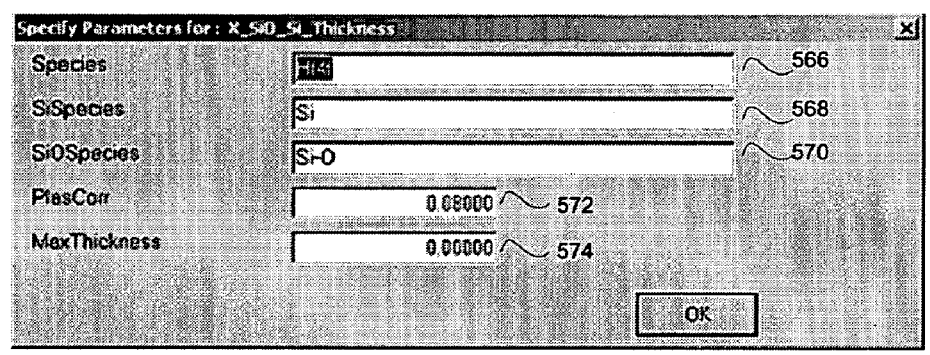

FIG. 5G illustrates a window 564 for specifying parameters for the X_SiO_Si_Thickness function. The X_SiO_Si_Thickness function is one of the preexisting functions that can be used to determine the thickness of certain layers of the structure 500. In the window 566, a user may input the photoelectron species found in the top layer of the structure 500 that is used to measure the thickness of the top layer of the structure 500. Here, the top layer is the hafnium oxide layer 506. The photoelectron species emitted by the hafnium oxide layer 506 is Hf4f. The thickness of the top layer may be needed to calculate the thickness of a layer beneath the top layer. In the window 568, the user inputs the name of the photoelectron species corresponding to silicon metal in the substrate. In the window 570, the user inputs the name of the photoelectron species corresponding to oxidized silicon in the top layer. In the window 572, the user inputs the plasmon correction, and in the window 574, the user inputs the largest thickness that can be measured in the top layer of the structure 500. The plasmon correction is used to correct for the fact that the silicon metal photoelectron signal loses energy to the plasmon in the silicon.

Other parameters may be added to the GUI, and some that are shown may be excluded. Additionally, the parameters shown may also be adjusted for photoelectron or elemental species not shown. For example, FIG. 5E shows the window 544 for adjusting EAL values for hafnium. Other windows may be used to adjust EAL values for oxygen or silicon.

Figure 5H:
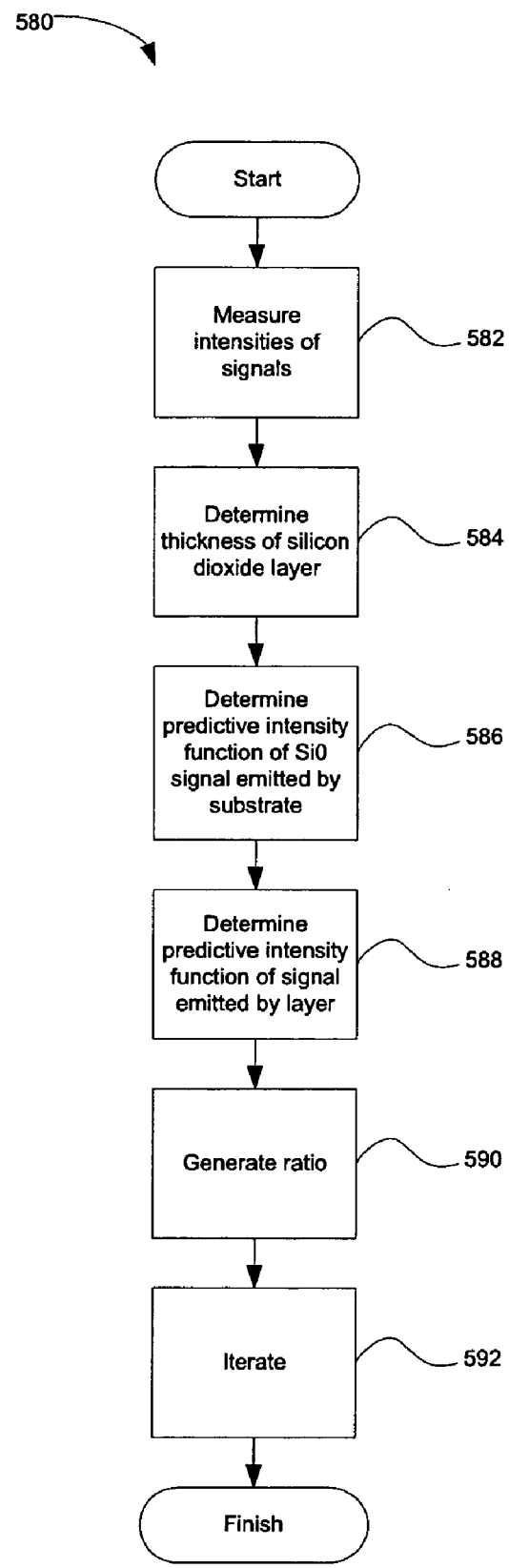
FIG. 5H is a flowchart describing a process for determining a thickness of the top layer of the structure.

FIG. 5H is a flowchart describing a process 580 for determining a thickness of the top layer of the structure 500. In this process 450, the thickness of the silicon dioxide layer 504 is first determined, and a ratio of photoelectrons emitted by the top layer 502 and photoelectrons emitted by the substrate 506 and attenuated by the silicon dioxide layer 504 and the top layer 502.

The following photoelectron species may be measured to determine the thickness of the layers 502 and 504. It is understood that other photoelectron species may also be used. The top layer 502 may comprise, for example, hafnium oxide. The photoelectron signal 575 measured here is of (for example) the Hf4f species. The photoelectron signal 576 measured from the silicon dioxide layer 404 (the "Si4+" species) is from the 2p orbital of the silicon atom and is influenced by the silicon-oxygen bond in the silicon dioxide layer 504. The photoelectron signal 577 emitted by the substrate 506 (the "Si0" species) is emitted from the 2p orbital of the silicon atom and is influenced by the silicon-silicon bond in the substrate 506.

In block 582, a measured intensity of the Hf4f signal 575, the Si4+ signal 576, and the Si0 signal 578 are determined using a process and equipment similar to those described above in FIG. 1A.

In the equations below, the thickness of the layer 502 is given as $t_{HfO2}$, the thickness of the silicon dioxide layer 504 is given as $t_{SiO2}$, the EAL of the Hf4f photoelectron species is given as $\lambda_{Hf4f(HfO2)}$, the EAL of the Si4+ photoelectron species is given as $\lambda_{Si2p(HfO2)}$ in $HfO_2$ and $\lambda_{Si2p(SiO2)}$ in $SiO_2$. The intensity of photoelectrons emitted from a thick (e.g., thicker than 10 nm) layer is given by $I_{infHf4f}$ and $I_{infSi4+}$ (for the Hf4f and Si2p photoelectron species, respectively). The measured intensity of the signal 575 of the Hf4f photoelectron species is I(Hf4f) and the measured intensity of the signal 576 of the Si2p species is I(Si2p).

In block 584, the thickness of the silicon dioxide layer 504 is determined. The thickness of the silicon dioxide layer is determined using the following equation (4):

$$t_{SiO2} = \sin(\alpha)\ln[(I(Si0)/I(Si4+))*k+1] \quad (4)$$

where α=an angle of the analyzer 212 relative to the surface of the structure 500, and k is the bulk material intensity (a constant that is dependent on the material used). The equation (4) is a known equation for determining a thickness of a silicon dioxide layer within a structure.

In block 586, a predictive intensity function of the Si0 signal 577 emitted by the substrate 506 is determined. Since the signal 577 emitted by the substrate 506 is attenuated by the layers 504 and 502, the predictive intensity function (shown in equation (5)) is of the form of the equation (2):

$$I(Si0) = I_{infSi} e^{\frac{-t_{HfO2}}{\lambda_{Si(HfO2)}}} \cdot e^{\frac{-t_{SiO2}}{\lambda_{Si(SiO2)}}} \quad (5)$$

Since the signal is attenuated through two layers, two attenuation factors (one for the hafnium oxide layer 502 and one for the silicon dioxide layer 504) are used.

In block 588, a predictive intensity function for a signal 575 of the Hf4f photoelectron species emitted by the layer 502 is determined. The layer 502 is the top layer of the structure 500, and therefore the equation (6) is of the form of the equation (1):

$$I(Hf4f) = I_{infHf} \cdot \left[1 - e^{\left(\frac{-t_{HfO2}}{\lambda_{Hf4f(1)}}\right)}\right] \quad (6)$$

In block 590, a ratio of the equations (5) and (6) is generated, as show in equation (7):

$$\frac{I(Si0)}{I(Hf4f)} = \frac{I_{infSi} \cdot e^{\frac{-t_{HfO2}}{\lambda_{Si(HfO2)}}} \cdot e^{\frac{-t_{SiO2}}{\lambda_{Si(SiO2)}}}}{I_{infHf} \cdot \left(1 - e^{\frac{-t_{HfO2}}{\lambda_{Hf(HfO2)}}}\right)} \quad (7)$$

In block 592, the equation (7) is iterated to determine the thickness of the layer 502.

Figure 6:
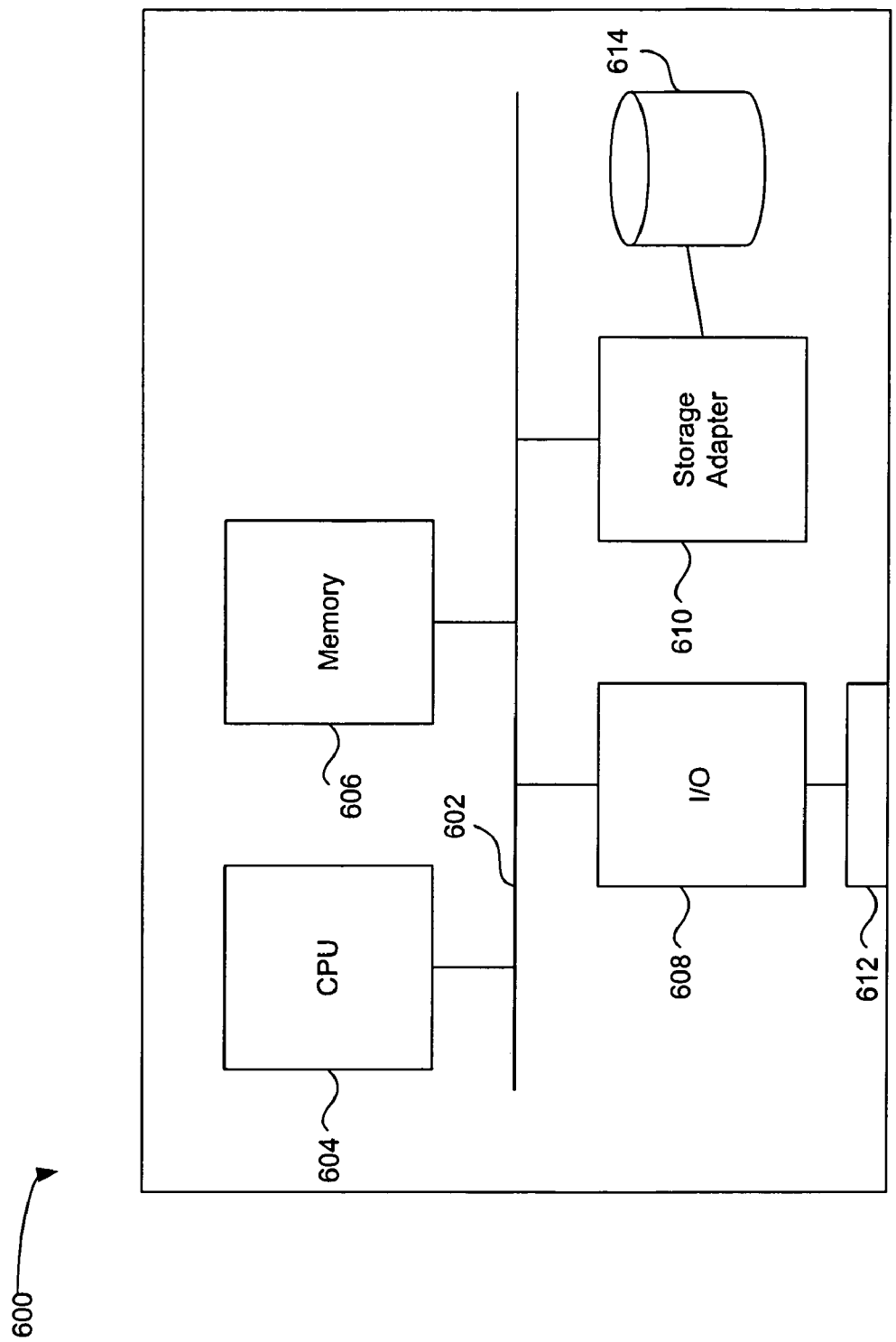
FIG. 6 illustrates a processing system for performing certain embodiments of the invention.

FIG. 6 illustrates a processing system 600 for performing certain embodiments of the invention. The processing system 600 may be used to implement the process 300, and may be representative of the processing system 116 described above. The processing system 600 may be a personal computer (PC) or other similar computing system.

The processing system 600 includes a bus 602 which may comprise one or several different buses. The bus 602 may include, for example, a peripheral component interface (PCI) bus. Attached to the bus are a central processing unit (CPU) 604, a memory 606, an input/output (I/O) adapter 608, and a storage adapter 610.

The CPU 604 may be any available processor, such as those manufactured by Intel® or Motorola®. The memory 606 may comprise one or more memories, including a random access memory (RAM) and a read only memory (ROM). The input/output adapter 608 may include a serial adapter such as a universal serial bus (USB) adapter including a USB port 612. The USB port 612 may be used to interface with the instrument 204. The I/O adapter may also include a video adapter and a keyboard interface to allow a user to input parameters and view results. The storage adapter 610 controls a drive 614. The drive 614 may be any appropriate type of storage, such as a magnetic hard drive or an optical drive. Instructions for executing certain embodiments of the invention may be stored on the drive 614 and be transferred to the memory 606 for execution. It is understood that the system 600 is only an example of one of many possible configurations of a processing system.

This invention has been described with reference to specific exemplary embodiments thereof. It will, however, be evident to persons having the benefit of this disclosure that various modifications and changes may be made to these embodiments without departing from the broader spirit and scope of the invention. The specification and drawings are accordingly to be regarded in an illustrative rather than in a restrictive sense.

What is claimed is:

1. A method for analyzing data from an instrument comprising:
   receiving raw data from the instruments and configuration data from a user including parameters to generate an algorithm;
   passing the raw data and the configuration data to an engine to generate the algorithm based on the parameters;
   receiving results from the engine based on the raw data, the configuration data, and the algorithm generated by the engine; and
   returning the results to the user,
   wherein passing the raw data and the configuration data comprises:
      packaging the raw data and the configuration data in a model; and
      transmitting the model to the engine,
   wherein packaging the raw data an the configuration data in a model comprises:
      generating a list of layers for the model including algorithms for determining a characteristic of a layer;
      generating a list of species for the model within the list of layers;
      generating a list of results including the results within the list of species; and
      generating a list of regions of the raw data.

2. The method of claim 1, further comprising:
   selecting the parameters based on elemental species within and a configuration of a structure measured by the instrument.

3. The method of claim 2, wherein selecting the parameters based on elemental species within and a configuration of a structure comprises:
   selecting the parameters based on a number of layers on a substrate and photoelectron species of the layers on the substrate.

4. The method of claim 1, wherein receiving raw data comprises:
   receiving counts of photoelectrons having a kinetic energy.

5. The method of claim 4, wherein receiving counts of photoelectrons having a kinetic energy comprises:
   generating photoelectrons using X-ray photoelectron spectroscopy (XPS).

6. The method of claim 1, wherein generating a list of layers for the model comprises:
   generating the list of layers including thickness algorithms for determining a thickness of the layer and concentration algorithms for determining an atomic concentration of the layer.

7. The method of claim 1, further comprising:
   generating a list of custom functions including a list of custom function parameters to execute the custom functions.

8. A method for determining characteristics of a layer on a substrate comprising:
   receiving raw data from an instrument measuring the layer and configuration data including parameters for determining a characteristic of the layer;
   passing the raw data and the configuration data to an engine to generate an algorithm to determine the characteristic of the layer;
   receiving results from the engine including the characteristic of the layer; and
   returning the results to a user;
   determining the parameters based on an elemental species of the layer and a number of other layers on the substrate; and
   determining the algorithm using other algorithms selected based on the parameters,
   wherein the other algorithms are predetermined based on known characteristics of photoelectron species and layers.

9. The method of claim 8, wherein the characteristic is selected from a group consisting of:
   a thickness of the layer, an atomic concentration of the layer, and a profile of the layer.

10. The method of claim 8, wherein passing the raw data and the configuration data to an engine comprises:
    packaging the raw data and the configuration data in a model; and
    transmitting the model to the engine.

11. The method of claim 10, wherein packaging the raw data and the configuration data in a model comprises:
    generating a list of layers for the model including algorithms for determining the characteristic of the layer;
    generating a list of species for the model within the list of layers;
    generating a list of results including the results within the list of species; and
    generating a list of regions of the raw data.

12. The method of claim 11, wherein generating the list of layers for the model comprises:
    generating the list of layers including thickness algorithms for determining a thickness of the layer and concentration algorithms for determining an atomic concentration of the layer.

13. The method of claim 11, further comprising:
    generating a list of custom functions including a list of custom function parameters to execute the custom functions.

14. A method for determining characteristics of layers on a substrate using photoelectron spectroscopy comprising:
    receiving raw data from an instrument including counts of photoelectrons;
    receiving configuration data from a user including parameters to determine an algorithm to determine a characteristic of a layer on the substrate;
    packaging the raw data and the configuration data in a model and passing the model to an engine;
    receiving results from the engine including the characteristic of the layer, wherein the characteristic is determined using the algorithm; and
    returning the results to the user,
    wherein packaging the raw data and the configuration data in the model comprises:
       generating a list of layers for the model including algorithms for determining the characteristic of the layer;
       generating a list of species for the model within the list of layers;
       generating a list of results including the results within the list of species; and
       generating a list of regions of the raw data.

15. The method of claim 14, wherein generating the list of layers for the model comprises:

generating the list of layers including thickness algorithms for determining a thickness of the layer and concentration algorithms for determining an atomic concentration of the layer.

16. The method of claim 14, wherein receiving raw data comprises:
receiving counts per minute of photoelectrons having a kinetic energy.

17. The method of claim 14, wherein the photoelectron spectroscopy is X-ray photoelectron spectroscopy.

18. The method of claim 14, further comprising:
generating a list of custom functions including a list of custom function parameters to execute the custom functions.

19. A machine readable medium having stored thereon executable program code which, when executed, causes a machine to perform a method for determining characteristics of a layer on a substrate, the method comprising:
receiving raw data from an instrument measuring the layer and configuration data including parameters for determining a characteristic of the layer;
passing the raw data and the configuration data to an engine to generate an algorithm to determine the characteristic of the layer;
receiving results from the engine including the characteristic of the layer;
returning the results to a user;
determining the parameters based on an elemental species of the layer and a number of other layers on the substrate; and
determining the algorithm using other algorithms selected based on the parameters,
wherein the other algorithms are predetermined based on known characteristics of photoelectron species and layers.

20. The machine readable medium of claim 19, wherein the characteristic is selected from a group consisting of:
a thickness of the layer, an atomic concentration of the layer, and a profile of the layer.

21. The machine readable medium of claim 19, wherein passing the raw data and the configuration data to an engine comprises:
packaging the raw data and the configuration data in a model; and
transmitting the model to the engine.

22. The machine readable medium of claim 21, wherein packaging the raw data and the configuration data in a model comprises:
generating a list of layers for the model including algorithms for determining the characteristic of the layer;
generating a list of species for the model within the list of layers;
generating a list of results including the results within the list of species; and
generating a list of regions of the raw data.

23. The machine readable medium of claim 22, wherein generating the list of layers for the model comprises:
generating the list of layers including thickness algorithms for determining a thickness of the layer and concentration algorithms for determining an atomic concentration of the layer.

24. The machine readable medium of claim 22, the method further comprising:
generating a list of custom functions including a list of custom function parameters to execute the custom functions.

* * * * *